US00PP28649P3

(12) United States Plant Patent
Layt

(10) Patent No.: US PP28,649 P3
(45) Date of Patent: Nov. 14, 2017

(54) ***ANIGOZANTHOS* PLANT NAMED 'KP03'**

(50) Latin Name: ***Anigozanthos* hybrid**
Varietal Denomination: KP03

(71) Applicant: Todd Anthony Layt, Clarendon (AU)

(72) Inventor: Todd Anthony Layt, Clarendon (AU)

( * ) Notice: Subject to any disclaimer, the term of this patent is extended or adjusted under 35 U.S.C. 154(b) by 58 days.

(21) Appl. No.: 14/999,394

(22) Filed: May 2, 2016

(65) Prior Publication Data

US 2016/0330892 P1 Nov. 10, 2016

(30) Foreign Application Priority Data

May 6, 2015 (AU) ..... 2015/097

(51) Int. Cl.
*A01H 5/02* (2006.01)

(52) U.S. Cl.
USPC ..... Plt./362

(58) Field of Classification Search
USPC ..... Plt./362
See application file for complete search history.

(56) References Cited

PUBLICATIONS

Google search on "*Anigozanthos*" and "kp03" using "Tools" to control for date. Search conducted on Aug. 10, 2017.*
Domus Nursery Catalogue List, downloaded from the Internet at Aug. 10, 2017, http://www.domusnursery.com.au/dom_catalogue.jsp?Searched=Y&CategoryId=&Text=anigozanthos &GroupBy=ALPHA.*
Domus Nursery—Stock List, downloaded using the Wayback Machine on Aug. 18, 2017, https://web.archive.org/web/20140310035512/http://www.domusnursery.com.au/dom_stocklist.jsp?Searched=&CategoryId=&Text= &GroupBy=ALPHA.*

* cited by examiner

*Primary Examiner* — Anne Grunberg
(74) *Attorney, Agent, or Firm* — Samuel R. McCoy, Jr.

(57) ABSTRACT

'KP03' is a distinctive cultivar of *Anigozanthos* hybrid plant which is characterized by the combination of a compact growth habit, broad foliage, excellent disease resistance, and an abundance of large golden yellow flowers. The new variety propagates successfully by division and tissue culture and has shown to be uniform and stable in the resulting generations from asexual propagation.

2 Drawing Sheets

Latin name of the genus and species: The Latin name of the genus and species of the novel variety disclosed herein is *Anigozanthos* hybrid.

Variety denomination: The inventive variety of *Anigozanthos* hybrid disclosed herein has been given the variety denomination 'KP03'.

BACKGROUND OF THE INVENTION

Parentage: 'KP03' is a seedling selection of unknown parentage which resulted from an open-pollination and seedling selection process carried out by the inventor at a commercial breeding facility in Clarendon, NSW, Australia. In 2010 and 2011, a number of *Anigozanthos* hybrid cultivars and a proprietary breeding line developed and owned by the same inventor, the seed parent, were grown in close proximity to one another in order to encourage open cross pollination. Cultivars included *Anigozanthos* hybrid 'Amber Velvet' (U.S. Plant Pat. No. 18,999), *Anigozanthos* hybrid 'Gold Velvet' (U.S. Plant Pat. No. 21,178), 'Regal Velvet' (not patented), and *Anigozanthos* hybrid 'Ruby Velvet' (not patented). In 2011, seeds were collected from the proprietary breeding line and germinated. The resulting seedlings were grown to maturity for further observation and, after the first flowering, a small number of plants were observed to exhibit a more compact growth habit and a greater number of inflorescences by comparison with the seed parent and each of the possible pollen parent cultivars. One progeny in particular was selected for commercialization in November of 2012 due to its broad foliage, compact growth habit and an abundance of inflorescences bearing large golden yellow flowers. This new and distinctive cultivar was given the name 'KP03'.

Asexual Reproduction: 'KP03' was first asexually propagated in November of 2012 by rhizome division in Clarendon, NSW, Australia and has since been asexually reproduced by meristematic tissue culture propagation. The distinctive characteristics of the inventive 'KP03' variety have proven to be stable through five generations and clones so produced maintain the distinguishing characteristics of the original plant.

SUMMARY OF THE INVENTION

The following traits have been repeatedly observed and represent the characteristics of the new cultivar. These characteristics, in combination, distinguish 'KP03' as a distinct cultivar of *Anigozanthos* hybrid:

1. 'KP03' exhibits broad foliage; and
2. 'KP03' exhibits a compact growth habit; and
3. 'KP03' exhibits a very floriferous flowering habit; and
4. 'KP03' exhibits large golden yellow flowers; and
5. 'KP03' exhibits high disease resistance.

BOTANICAL DESCRIPTION OF THE PLANT

Figure 1:
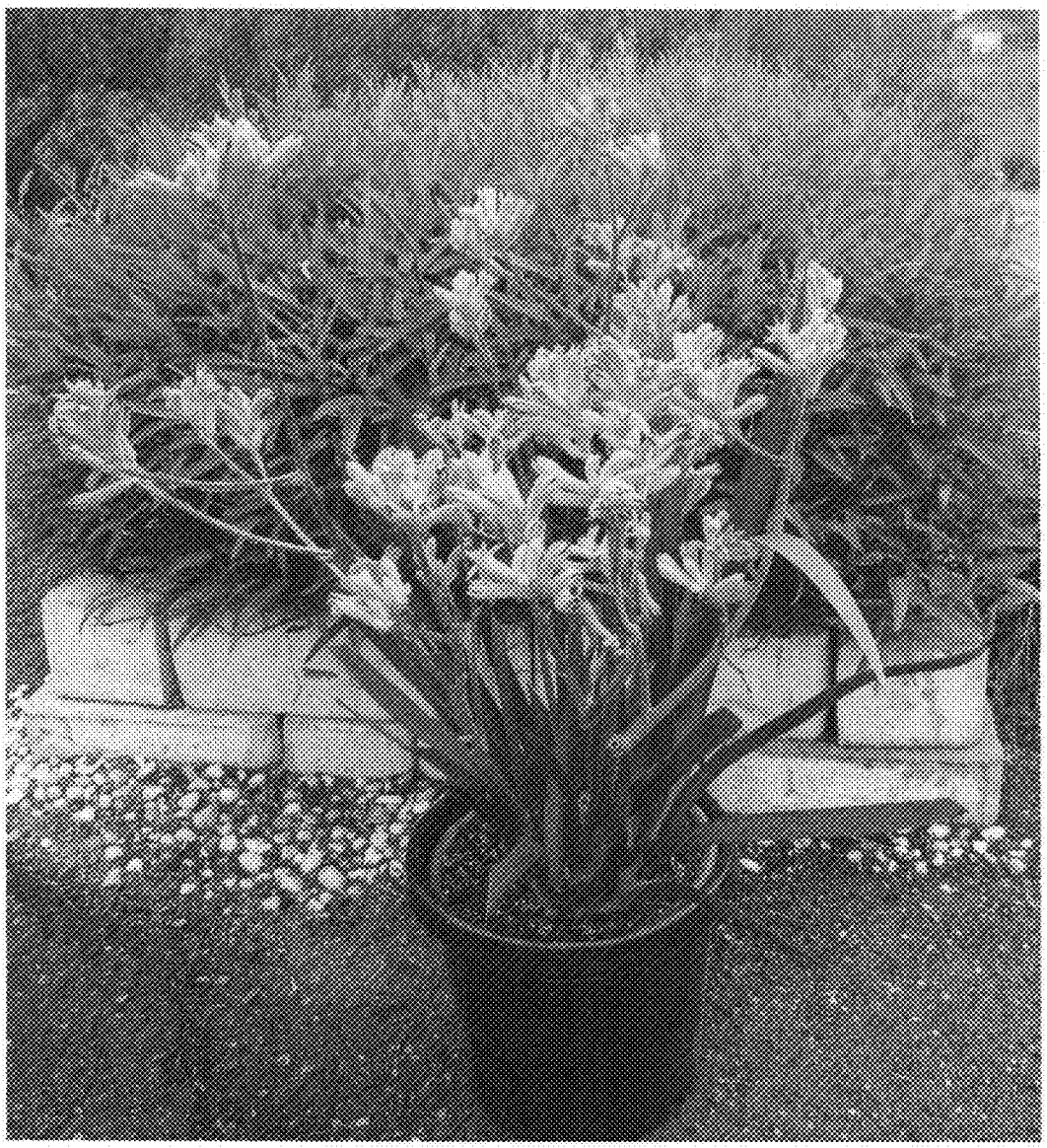
FIG. 1 illustrates, as true as is reasonably possible to obtain in color photographs of this type, an exemplary 'KP03' specimen. These 24 month old plants were grown outdoors in 300 mm nursery containers at a commercial plant breeding facility in Clarendon, NSW, Australia.
Figure 2:
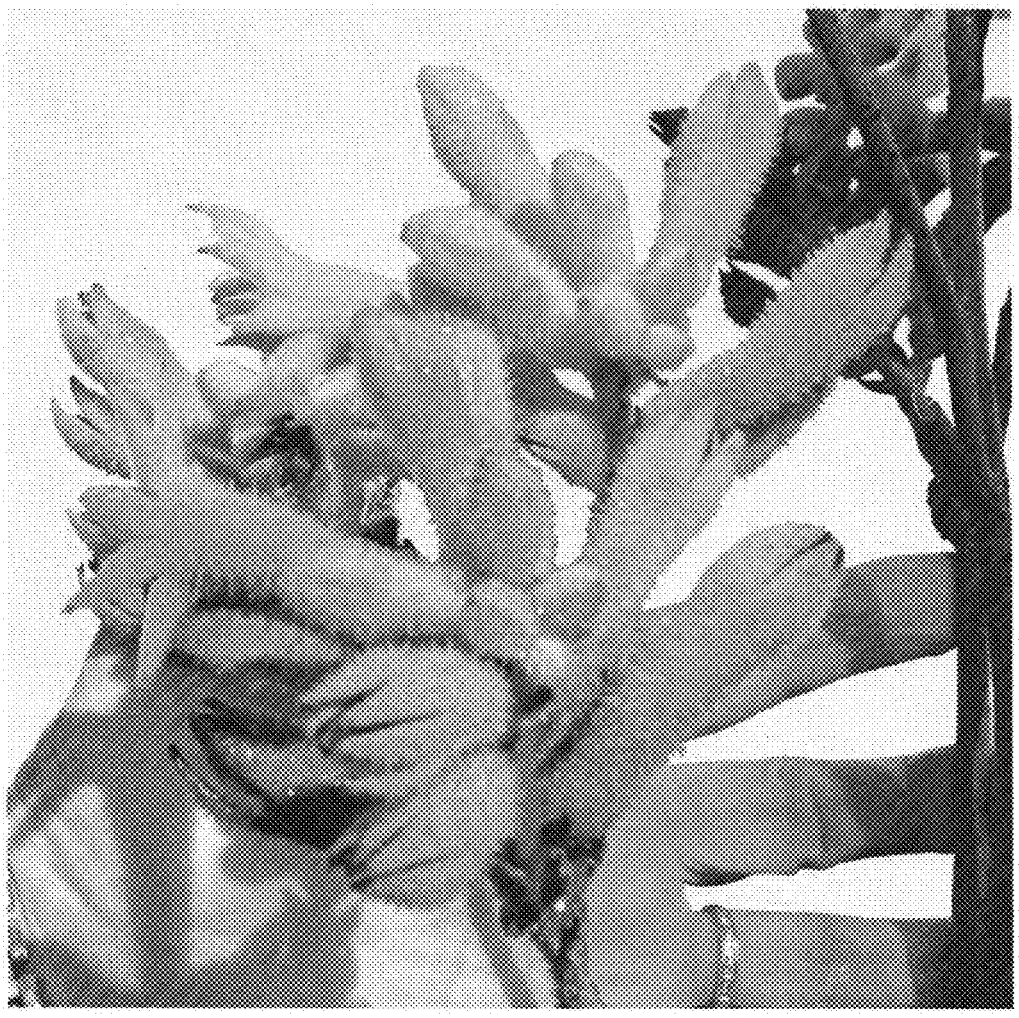
FIG. 2 illustrates, as true as is reasonably possible to obtain in color photographs of this type, exemplary buds and flowers of 'KP03'.

The following is a detailed botanical description of a new and distinct variety of a *Anigozanthos* hybrid ornamental plant known as 'KP03'. Plant observations were made on plants grown in Clarendon, NSW, Australia. Unless indicated otherwise, the descriptions disclosed herein are based upon observations made in September 2015 of 36 month old 'KP03' plants. These plants were grown outdoors, in full sun, in 300 mm nursery pots filled with soilless potting media, maintained with granular slow release fertilizer and regularly watered with overhead irrigation. No pest and disease measures were taken.

Those skilled in the art will appreciate that certain characteristics will vary with older or, conversely, younger plants. 'KP03' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2001 Edition. Note that generic color descriptions such as 'green' do not exist in the R.H.S. charts and the corresponding R.H.S. colors are quoted.

A botanical description of 'KP03' and comparisons with the seed parent and several similar varieties of common knowledge are provided below.

General plant description:

*Plant habit*.—Strap-leaf herbaceous perennial with erect foliage; rhizomatous plant forming a clump.

*Height*.—50 cm.

*Width*.—50 cm.

*Hardiness*.—USDA Lone 9 to 11.

*Propagation*.—Propagation is accomplished by dividing the rhizomatous crown of the plant and also by way of meristematic tissue culture propagation.

*Crop time*.—Time to initiate root development is approximately 3 weeks, from division; approximately 6 weeks to produce a marketable rooted cutting.

*Environmental tolerances*.—Tolerates full sun to partial shade, poor to fertile soils, and semi-regular watering or rainfall.

*Pest and disease susceptibility or resistance*.—No known pest or disease problems; excellent resistance to ink spot disease.

Roots: A network of thick, fleshy rhizomes with freely-branched fibrous roots.

Stems:

*Branching habit*.—Acaulescent, rhizomatous plant with shoots emerging upright at close to 90 degrees from the soil surface.

Foliage:

*Foliage abundance*.—Moderately abundant.

*Shape*.—Linear.

*Division*.—Simple.

*Arrangement*.—Equitant.

*Attachment*.—Radical.

*Apex*.—Subulate.

*Margins*.—Entire.

*Mature leaf dimensions*.—23 mm wide and 500 mm long, on average. The leaf thickness is 1.3 mm, on average.

*Juvenile foliage color, adaxial & abaxial surfaces*.—Yellow-green, RHS 146A.

*Mature foliage color, adaxial & abaxial surfaces*.—Yellow-green, RHS 146A.

*Venation*.—Parallel.

*Vein color, adaxial surfaces*.—Yellow-green, RHS 146A.

*Vein color, abaxial surfaces*.—Yellow-green, RHS 146A.

*Texture, adaxial surface*.—Smooth and glabrous.

*Texture, abaxial surface*.—Smooth and glabrous.

Inflorescence:

*Type*.—Compound one-sided raceme.

*Natural flowering season*.—August to October in NSW, Australia.

*Overall dimensions*.—Up to 1000 mm long and 300 mm wide.

*Inflorescence attitude*.—Erect.

*Quantity*.—Medium to high; 7 inflorescence observed.

*Peduncle*.—Dimensions — Up to 1000 mm long and 10 mm in diameter. Strength — Medium. Texture — Densely pubescent. Hairs are yellow-white, RHS 158D, on the lower portion and red, RHS 45A, on the upper portion. Color — Yellow-green, RHS 146A.

Bud:

*Dimensions*.—Approximately 38 mm long and 8.5 mm at the widest and 5.6 mm at the narrowest; 4.9 mm at the ovary.

*Bud shape*.—Tubular and globose at the distal end.

*Bud color*.—Yellow, RHS 12A, with intonations of red, RHS 45A at the distal end.

Flower:

*Quantity*.—Abundant; greater than 130 flowers per inflorescence.

*Shape*.—Tubular.

*Persistence*.—Non-persistent.

*Lastingness*.—7 days.

*Aspect*.—Semi-erect.

*Fragrance*.—Non-fragrant.

*Pedicels*.—Dimensions — 8 mm long and 2.1 mm in diameter. Attitude — Semi-erect. Strength — Medium. Texture — Densely pubescent; hairs are red, RHS 45A. Color — Yellow-green, RHS 146A.

*Perianth*.—General description — Perianth is comprised of six tepals fused into a tube with tepal lobes at the distal end. Dimensions — Approximately 10 mm in diameter and 43 mm deep. Tepal lobe apex — Acute. Tepal lobe reflex — Strongly reflexed. Tepal lobe margin — Entire; not undulated. Texture and pubescence — Pubescent. Color when opening, inner surface — Yellow-green, RHS 144A. Color when opening, proximal end of outer surface — Red, RHS 45A. Color when opening, distal end of outer surface — Yellow, RHS 5A. Color when fully opened, inner surface — Yellow-green, RHS 144A. Color when fully opened, proximal end of outer surface — Red, RHS 45A. Color when fully opened, distal end of outer surface — Yellow, RHS 5A.

*Floral bract*.—Quantity — One. Shape — Subulate. Apex — Apiculate. Base — Flat at fusion with the pedicel. Texture — Densely pubescent. Dimensions — Approximately 12 mm long and 5.5 mm wide at the base. Color, inner surface — Yellow-Green, RHS 144A. Color, outer surface — Yellow, RHS 9A, with slight intonations of red, RHS 45A.

Reproduction organs:

*Stamens*.—Quantity — Six adnate stamens. Filament — Approximately 40 mm long and 0.25 in diameter; color is yellow, RHS 7D. Anther — Two-lobed; oblong to linear; basifixed; approximately 3.5 mm long and 1.0 mm in diameter; color is yellow, RHS 14B. Pollen — Low amount of pollen present; color is closest to yellow, RHS 11C.

*Pistil*.—Quantity — One. Dimensions — Approximately 40 mm long and 0.5 in diameter. Stigma — Linear; approximately 38.5 mm long; color is green-white, near 157A. Style — Curved; 1.5 mm tall and 1 mm in diameter; color is yellow, RHS 14B. Ovary — Position is superior; 5 mm tall and 5 mm in diameter; color is red, RHS 45A.

Fruit and seed:

*Fruit*.—Ovoid capsules are 10 mm long and 8 mm in diameter; color is red, RHS 45A, and fade to brown, RHS 200.

*Seed*.—Irregular, angular; approximately 1 mm in diameter; color is dark grey to black, nearest to RHS 202B.

COMPARISONS WITH THE PARENT PLANT

Plants of the new cultivar 'KP03' may be distinguished from the seed parent, a proprietary *Anigozanthos* hybrid breeding line, by the quantity of flowers produced. 'KP03' exhibits a very high flower count, whereas the seed parent exhibits a low flower count.

COMPARISONS WITH THE MOST SIMILAR VARIETY OF COMMON KNOWLEDGE

Plants of the new cultivar 'KP03' may be distinguished from the commercial variety, *Anigozanthos* hybrid 'KP02' (U.S. plant patent application having application Ser. No. 14/999,393 filed concurrently with the instant application), by the following combination of characteristics:

1. 'KP03' exhibits broad leaves that are approximately 23 mm wide, whereas 'KP02' exhibits narrow leaves, approximately 14 mm wide.
2. 'KP03' is a larger plant at approximately 50 cm tall and 50 cm wide, whereas 'KP02' is approximately 40 cm tall and 40 cm wide.
3. 'KP03' exhibits a long perianth tube which is approximately 43 mm deep, whereas 'KP02' exhibits a shorter perianth tube that is approximately 30 mm deep.
4. 'KP03' exhibits more than 130 flowers per inflorescence, whereas 'KP02' exhibits approximately 40 flowers per inflorescence.

That which is claimed is:

1. A new and distinct variety of *Anigozanthos* hybrid plant named 'KP03', substantially as described and illustrated herein.

* * * * *